(12) United States Patent
Forte et al.

(10) Patent No.: US 6,417,350 B1
(45) Date of Patent: Jul. 9, 2002

(54) PREPARATION OF (11β,16β)-21-(3-CARBOXY-1-OXOPROPOXY)-11-HYDROXY-2'-METHYL-5'H-PREGNA-1,4-DIENO [17,16-D]OXAZOLE-3,20-DIONE

(75) Inventors: Luigi Forte; Calogero Cancellieri, both of Brindisi (IT)

(73) Assignee: Aventis Bulk S.p.A., Milan (IT)

( * ) Notice: Subject to any disclaimer, the term of this patent is extended or adjusted under 35 U.S.C. 154(b) by 0 days.

(21) Appl. No.: 09/488,035

(22) Filed: Jan. 20, 2000

Related U.S. Application Data

(63) Continuation of application No. 09/077,729, filed as application No. PCT/EP96/05391 on Dec. 4, 1996, now abandoned.

(30) Foreign Application Priority Data

Dec. 13, 1995 (EP) ............................................. 95119627

(51) Int. Cl.[7] ................................................. C07J 71/00
(52) U.S. Cl. ......................................................... 540/56
(58) Field of Search ........................................... 540/56

(56) References Cited

U.S. PATENT DOCUMENTS 4,440,764 A * 4/1984 Nathansohn et al. ........ 424/241

* cited by examiner

Primary Examiner—Brenda Coleman
(74) Attorney, Agent, or Firm—Julie Anne Knight

(57) ABSTRACT

A process for preparing the compound (11β,16β)-21-(3-CARBOXY-1-OXOPROPOXY)-11-HYDROXY-2'-METHYL-5'H-PREGNA-1,4-DIENO(17,16-D)OXAZOLE-3,20-DIONE which comprises reacting the compound (11β,16β)-11,21-DIHYDROXY-2'-METHYL-5'H-PREGNA-1, 4-DIENO(17,16-D)OXAZOLE-3,20-DIONE with succinic anhydride in a ($C_1$–$C_4$) alkyl ester of a ($C_{1–C4}$) carboxylic acid as solvent, in the presence of a basic catalyst.

11 Claims, No Drawings

PREPARATION OF (11β,16β)-21-(3-CARBOXY-1-OXOPROPOXY)-11-HYDROXY-2'-METHYL-5'H-PREGNA-1,4-DIENO [17,16-D]OXAZOLE-3,20-DIONE

This application is a continuation of application Ser. No. 09/077,729, now abandoned, which is a national stage entry under 35 U.S.C. §371 of PCT/EP96/05391, filed Dec. 4, 1996.

The present invention refers to a new process for preparing the compound of formula I

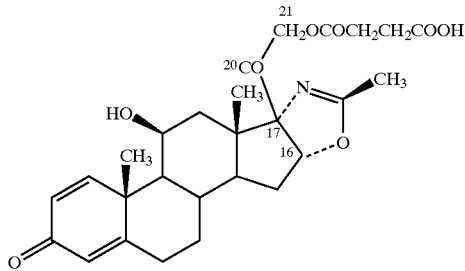

Formula I i.e. (11β,16β)-21-(3-carboxy-1-oxopropoxy)-11-hydroxy-2'-methyl-5'H-pregna-1,4-dieno(17,16-d)oxazole-3,20-dione.

The above compound is a water soluble ester of deflazacort (INN—International Nonproprietary Name), wherein the acetate moiety on the C-21 of deflazacort is substituted by an hemisuccinate moiety.

Deflazacort is a compound employed in therapy since some years as a calcium-sparing corticoid agent.

These compounds belong to the more general class of pregneno-oxazolines, for which anti-inflammatory, glucocorticoid and hormone-like pharmacological activities are reported. Examples of compounds of the above class, comprising deflazacort, are disclosed in U.S. Pat. No. 3,413,286.

EP-B-322630 discloses a fermentation process for preparing the (11β,16β)-11,21-dihydroxy-2'-metyl-5'H-pregna-1,4-dieno(17,16-d)oxazole-3,20-dione, which corresponds to the compound of formula I bearing a hydroxy group in place of the hemisuccinate moiety at the position 21. This compound is referred to in the above patent as 11β-21-dihydroxy-2'methyl-5'βH-pregna-1,4-dieno(17,16-d) oxazoline-3,20-dione and can be represented by the following formula II:

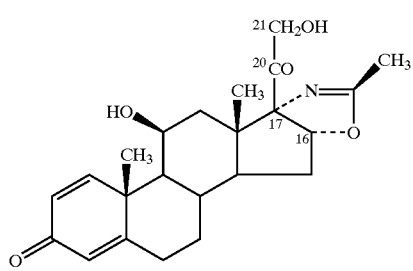

II

U.S. Pat. No. 4,440,764 discloses the compound of formula I, with the name 11β-21-dihydroxy-2'-methyl-5'βH-pregna-1,4-dieno[17,16-d]oxazole-3,20-dione 21-hemisuccinate, and a process for its preparation, which comprises reacting the compound of formula II with a molar excess of succinic anhydride (from 0.1 to 5 times) in an organic solvent and in the presence of a basic catalyst.

Among the cited organic solvents are halogenated lower aliphatic hydrocarbons, acetone, ethyl acetate, dimethylformamide and acetonitrile; as the basic catalyst, 4-(N,N-diethylamino)pyridine is specifically mentioned; alternatively, organic solvents may be employed which act both as reaction solvents and basic catalysts, such as pyridine, collidine, picoline and mixtures thereof. The product can be recovered by washing the reaction mixture with an acidic solution and then crystallizing the end product from a suitable solvent.

In particular, methylene chloride can be employed as the organic solvent and 4-(N,N-diethylamino)pyridine as the catalyst; after the reaction is completed, the reaction mixture is then washed with aqueous 1 HCl and water and then diluted with toluene. The reaction solvent is distilled off and the product crystallizes in toluene upon cooling.

It has now been found that, by using a ($C_1$–$C_4$) alkyl ester of a ($C_1$–$C_4$) carboxylic acid as the reaction solvent, the same reaction solvent can surprisingly be used also for the crystallization of the end-product. The main advantages are a simplification of the preparation procedure and higher yields with respect to the prior art. Furthermore, these solvents, particularly ethyl acetate, are solvents widely accepted in industrial preparations, for what concerns the security, industrial hygiene and environment protection.

Although all of the other solvents known in the art are good reaction solvents, allowing the quantitative conversion of the compound of formula II into the compound of formula I, none of them is suitable also for crystallizing the final product. For instance, the compound of formula I is too soluble in halogenated lower aliphatic hydrocarbons (such as methylene chloride) and thus may not be crystallized from those solvents. Likewise, direct crystallization from solvents like dimethylformamide or acetonitrile is not possible, due to the high solubility of the above compound in these solvents. On the other side, the direct crystallization from acetone gives very poor yields, while a considerable amount of impurities co-crystallize with the desired product.

Thus, the process of the invention comprises reacting the compound of formula II with succinic anhydride in a ($C_1$–$C_4$)alkyl ester of a ($C_1$–$C_4$) carboxylic acid in the presence of a basic catalyst.

The starting material of formula II is obtained according to the procedures known in the art, for instance according to the fermentation process disclosed in the above cited EP-B-322630, here incorporated by reference. Said patent discloses a fermentation process for obtaining the compound of formula II, wherein a 2'-methyl-4-pregnen-21-ol-[17α, 16α-d-]oxazolinyl-3,20-dione is contacted with a sequentially growing mixed culture of a Curvularia strain and an Arthrobacter strain.

Examples 1 and 2 of EP 0 322 630 B1 disclose the following:

EXAMPLE 1

Sequential growth of *C. lunata* and *A. simplex*

I) Slant Media
  Sabouraud medium (for *C. lunata*)
  Antibiotic Agar No. 1 (for *A. simplex*)

II) Vegetative and Pre-culture Media
  a) for *C. lunata*

|   |   |
|---|---|
| Soybean meal | 13 g/l |
| KH$_2$PO$_4$ | 5 g/l |
| Dextrose | 10 g/l |
| Peptone | 5 g/l | pH adjusted to 6.5–7.5 before autoclaving b) for *A. simplex*

|   |   |
|---|---|
| Dextrose | 1.0 g/l |
| Soybean Meal | 5.0 g/l |
| Peptone | 5.0 g/l |
| Basamin Busch | 3.0 g/l |
| KH$_2$PO$_4$ | 5.0 g/l |
| NaCl | 5.0 g/l |
| Silicone | 0.1 m/l | pH adjusted to 6.5–7.5 before autoclaving.

III) Fermentation Media

A fermentation medium having the same composition of the pre-culture medium for *C. lunata* reported above.

IV) Fermentation Procedure

The slants are used to separately inoculate 500 ml flasks which are cultured at about 28° C. for about 12–24 h (*C. lunata*) or 18–36 h (*A. simplex*) in the presence of 100 ml of the vegetative media indicated above. These inocula are used in the procedure described below:

Aliquots (about 1 to 5%) of the culture of *C. lunata* obtained above are transferred in a 8 liter fermentor containing the above reported fermentation medium and cultivated for about 24 h at 29–32° C.

Then 4 g of 2'-methyl-4-pregnen-21-ol-[-17alpha, 16alpha-d]-oxazolinyl-3,20-dione are added and the fermentation is continued until about 36–72 h from the inoculum.

Afterwards, the 18–36 h culture of *A. simplex* is added thereto and the fermentation is continued for further 40–55 h.

The reaction course is monitored as known in the art by TLC or preferably HPLC by following the disappearance of the starting material and/or appearance of the final product. As a further control, the appearance/disappearance of intermediates can also be followed. HPLC conversion yield: 70–75%.

EXAMPLE 2

Recovery

After 40–55 h from the addition of *A. simplex*, the transformation can be generally considered as completed and the fermentation can be worked up to isolate the desired compound of formula I.

The fermentation mixture is separated by filtration, the mycelium is repeatedly washed with chloroform and the filtrate is extracted with chloroform (3×1 L). The combined chloroform washing and extracts are partially concentrated under reduced pressure and decolorized with charcoal. Then they are concentrated to an oily residue. On adding petroleum ether, a precipitate forms which is washed with ether (3 times) and collected by filtration giving 3 g of 2'-methyl-1,4-pregnadien-21-ol-[17alpha, 16alpha-d]oxazolinyl-3,20-dione that, has the following formula:

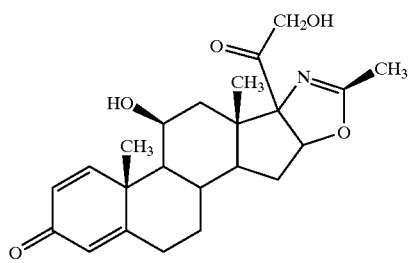

More in particular, according to a preferred embodiment, the above compound is added to a growing culture of *C. lunata* NRRL 2380 in a suitable fermentation medium after 12–24 hours from inoculum, and, after 48–72 hours from inoculum, a growing culture of *A. simplex* ATCC 6946 of 18–36 hours is added to the mixture and further cultivated for 40–55 hours; the fermentation is carried out under submerged conditions, temperature is kept between 27° C. and 32° C. and pH between 6 and 8; the fermentation product of formula II is recovered according to procedures known in the art.

Examples of (C$_1$–C$_4$)alkyl esters of a (C$_1$–C$_4$) carboxylic acids are the following: methyl, ethyl, propyl, iso-propyl, butyl, 2-methylpropyl or t-butyl formiate; methyl, ethyl, propyl, iso-propyl, butyl, 2-methylpropyl or t-butyl acetate; methyl, ethyl, propyl, iso-propyl, butyl, 2-methylpropyl or t-butyl propionate; methyl, ethyl, propyl, iso-propyl, butyl, 2-methylpropyl or t-butyl butirrate; methyl, ethyl, propyl, iso-propyl, butyl, 2-methylpropyl or t-butyl iso-butirrate. Particularly preferred is ethyl acetate.

The reaction temperature may vary from about 0° C. to 60° C.; preferably it will be in the range from 15° C. to 35° C., particularly preferred being room temperature.

The succinic anhydride is preferably reacted with the compound of formula II in a molar excess with respect to the stoichometric ratio; preferably, the molar ratio between the compound of formula II and succinic anhydride is from about 1:2 to about 1:5, particularly preferred being a molar ratio of about 1.0:2.5.

Basic catalysts useful in the present process are tertiary organic aliphatic or alicyclic amines such as trimethylamine, triethylamine (TEA), N-methyl pyrrolidine or heterocyclic bases such as pyridine, 4-(N,N-dimethylamino)-pyridine, 4-(N,N-diethylamino)-pyridine, collidine, picoline, and the like. Preferably, TEA is employed. The amount of catalyst will depend from the specific catalyst employed; in general it will be from about 0.1 to about 3 times the molar amount of the compound of formula II. Preferably its molar amount is from about equimolar to 2 times the molar amount of the compound of formula II; in particular, when the molar ratio between the compound of formula II and succinic anhydride is about 1.0:2.5 and TEA is the selected catalyst, its molar amount is about 1.5 times the molar amount of the compound of formula II.

At room temperature, the reaction is completed in about 18–30 hours. In any case the reaction course can be easily followed according to the standard techniques known in the art, such as by HPLC or TLC usually by following the formation of the final product. Thus, on the basis of the results of these assays, the skilled man is able to evaluate when to stop the reaction and begin the recovery of the desired product.

The reaction product is then recovered according to the standard procedures known in the art, which would allow the recovery of the compound of formula I from the same solvent used for the reaction.

For instance, the reaction mixture is preferably washed with an aqueous acid solution at a pH of about 2.0–3.5 (e.g with diluted mineral acids such as chloridric, sulfuric or phosphoric acid), the organic phase is separated, filtered and then the end-product is recovered, preferably by precipitation upon concentration of the filtered solution to small volume.

For better illustrating the invention, the following examples are given.

EXAMPLE 1

Preparation of (11β,16β)-21-(3-carboxy-3-oxopropoxy)-11-hydroxy-2'-methyl-5'H-pregna-1,4-dieno[17,16-d]oxazole-3,20-dione.

Recovery and Purification of (11β,16 β)-21-(3-CARBOXY-1-OXOPROPOXY)-11-HYDROXY-2'-METHYL-5'H-PREGNA-1,4-DIENO (17,16-D) OXAZOLE-3,20-DIONE.

When the reaction of Example 1 is completed, 100 ml of water are added and the pH is adjusted at a value of about 3 with 10% (w/w) sulfuric acid.

The aqueous layer is discarded and the organic layer is filtered and concentrated to a small volume. The suspension is kept at 5° C. for 2 hours; after filtration and drying, 11.2 g of crystalline product are obtained. By further concentrating the mother liquors to a smaller volume, further 0.8 g of product are obtained, for a total of 12.0 g and an overall yield above 98%.

The above product (12.0 g) is then suspended in 240 ml of apyrogen water. The suspension is kept under stirring at 35° C. for about 2 hours, cooled at 5° C. for about 1 hour and the solid is collected by filtration. After washing with apyrogen water and drying, 11.1 g of (11β,16β)-21-(3-carboxy-1-oxopropoxy)-11-hydroxy-2'-methyl-5'H-pregna-1,4-dieno-(17,16-d) oxazole-3,20-dione are obtained (yield 91%, purity>98%).

What is claimed is:

1. A process for preparing the compound (11β,16β)-21-(3-carboxy-1-oxopropoxy)-11-hydroxy-2'-methyl-5'H-pregna-1,4-dieno(17,16-d)oxazole-3,20-dione of Formula I Formula I which comprises (a) reacting the compound (11β,16β)-11,21-dihydroxy-2'-methyl-5'H-pregna-1,4-dieno(17,16-d)oxazole-3,20-dione of Formula II Formula II with succinic anhydride in a ($C_1$–$C_4$) alkyl ester of a ($C_1$–$C_4$)carboxylic acid as the solvent, in the presence of a basic catalyst, (b) washing the obtained reaction mixture with an aqueous acid solution at a pH of about 2.0–3.5, and (c) separating the organic phase, filtering and concentrating the reaction mixture to a small volume to precipitate the compound of Formula I.

2. The process according to claim 1 wherein the solvent is ethyl acetate.

3. The process according to claim 1 or 2 wherein the basic catalyst is selected from the group consisting of trimethylamine, triethylamine, N-methyl-pyrrolidine, pyridine, 4-(N,N-dimethylamino)pyridine, 4-(N,N-diethylamino)pyridine, collidine, and picoline.

4. The process according to claim 1 or 2 wherein the basic catalyst is triethylamine.

5. The process according to claim 1 wherein the reaction temperature is from 0° C. to 60° C.

6. The process according to claim 1 wherein the reaction temperature is from 15° C. to 35° C.

7. The process according to claim 1 wherein the molar ratio between the compound of Formula II and succinic anhydride is from 1:2 to 1:5.

8. The process according to claim 1 wherein the molar ratio between the compound of Formula II and succinic anhydride is about 1:2.5.

9. The process according to claim 1 wherein the amount of basic catalyst is from 0.1 to 3 times the molar amount of the compound of Formula II.

10. The process according to claim 1 wherein the amount of basic catalyst is from equimolar to 2 times the molar amount of the compound of Formula II.

11. The process according to claim 1 wherein the aqueous acid solution is a solution of a diluted mineral acid.

* * * * *